United States Patent [19]

Davis et al.

[11] Patent Number: 4,673,509

[45] Date of Patent: Jun. 16, 1987

[54] BIOCIDAL WATER TREATMENT

[75] Inventors: Keith P. Davis, Bromsgrove; Robert E. Talbot, Cannock, both of England

[73] Assignee: Albright & Wilson Limited, Warley, England

[21] Appl. No.: 644,783

[22] Filed: Aug. 27, 1984

[30] Foreign Application Priority Data

Aug. 26, 1983 [GB] United Kingdom ............... 8323025
Dec. 16, 1983 [GB] United Kingdom ............... 8333787

[51] Int. Cl.$^4$ ............................................. C02F 5/14
[52] U.S. Cl. ...................................... 210/699; 71/67; 162/161; 210/700; 210/755; 210/764; 514/76; 514/129; 514/139
[58] Field of Search .................... 71/67; 162/161, 190; 210/755, 764, 699, 700, 728; 252/106, 107; 260/502.4 R, 502.4 P; 422/28; 514/76, 118, 129, 139

[56] References Cited

U.S. PATENT DOCUMENTS

| | | | |
|---|---|---|---|
| 2,428,329 | 9/1947 | Ham et al. ............................ | 210/764 |
| 3,087,836 | 4/1963 | Dearborn ............................ | 162/159 |
| 3,223,513 | 12/1965 | Geary .................................. | 514/129 |
| 3,236,676 | 2/1966 | Coates et al. ...................... | 427/341 |
| 3,281,365 | 10/1966 | Moedritzer ......................... | 424/70 |
| 3,294,632 | 12/1966 | Wagner .............................. | 514/139 |
| 3,364,107 | 1/1968 | Berenson et al. ................... | 210/764 |
| 3,664,807 | 5/1972 | Redmore ............................ | 422/7 |
| 3,917,476 | 11/1975 | Kerst et al. ........................ | 71/67 |
| 3,998,754 | 12/1976 | Oswald .............................. | 71/67 |
| 4,017,610 | 4/1977 | Baker ................................. | 422/28 |
| 4,089,893 | 5/1978 | Carr ................................... | 210/699 |
| 4,554,367 | 11/1985 | Wehner et al. .................... | 71/86 |

FOREIGN PATENT DOCUMENTS

| | | | |
|---|---|---|---|
| 0066544 | 12/1982 | European Pat. Off. ........... | 210/764 |
| 906314 | 9/1962 | United Kingdom . | |
| 935098 | 8/1963 | United Kingdom . | |
| 938989 | 10/1963 | United Kingdom . | |
| 1203268 | 8/1970 | United Kingdom . | |
| 2112370 | 7/1983 | United Kingdom . | |

Primary Examiner—Peter Hruskoci
Attorney, Agent, or Firm—Frishauf, Holtz, Goodman & Woodward

[57] ABSTRACT

The growth of microbiological contaminants in industrial cooling and process waters and in aqueous based products, susceptible to microbiological spoilage on storage, is inhibited by the presence of a phosphorus compound having a hydroxy alkyl group directly attached to the phosphorus atom, such as tetrakis hydroxy methyl phosphonium sulphate.

14 Claims, No Drawings

BIOCIDAL WATER TREATMENT

This invention relates to the treatment of water to control the growth of aquatic microorganisms therein.

Aquatic microorganisms, in particular bacteria such as *Pseudomonas aeruginosa*, fungi such as Oscillatoria, and yeasts such as *Sacharomyces cerebisiae* grow in a variety of water systems such as industrial plant, chemical plant or steel manufacture, brewing, power generation or paper making plant, marine engines, central heating systems, and water used for oil field injection, or for the manufacture of aqueous based prodcuts. The organisms cause corrosion and/or fouling. Growth of these organisms may be controlled by treatment with oxidizing biocides such as chlorine or with inorganic biocides such as copper salts or with organic biocides, including quaternary ammonium or phosphonium compounds, with one or more long chain alkyl groups. A problem with such quaternary compounds is that such compounds give rise to foaming of the water.

We have discovered that phosphines or phosphonium compounds with 1 or more hydroxyalkyl groups attached to each phosphorus atom are highly effective at controlling the aquatic microorganisms. In particular such phosphines or phosphonium compounds are highly cost effective and are effective in the absence of long chain alkyl groups, which give rise to foaming problems in biocides of the prior art. We have additionally discovered that, at least under conditions of acid pH, the hydroxy alkyl phosphorus compounds exhibit valuable oxygen scavenging activity.

The present invention provides a method of treating water systems containing aquatic microorganisms or susceptible to infection therewith, which method comprises adding to said water at least one phosphorus compound containing at least one hydroxyalkyl group attached directly to a phosphorus atom.

The phosphorus compound may contain one phosphorus atom and may then be of formula $[HORPR'_nO_m]_yX_x$ wherein n is 2 or 3; m is 0 or 1 such that $(n+m)=2$ or 3; x is 0 or 1 such that $(n+x)=2$ or 4; y is equal to the valency of X; R is an alkylene group of 1 to 4, preferably 1, carbon atoms with the hydroxy group attached to the 1, 2, 3 or 4 numbered carbon atom; each R' may be the same or different and represents an alkyl or alkenyl group, preferably of 1-4 carbon atoms, or more usually a group of formula HOR—, wherein R is as defined above; and X is anion such that the phosphorus compound is water soluble. Thus the (—ROH) group may be a 1-, or 2-hydroxyalkyl group e.g. a hydroxy methyl, 1 or 2 hydroxy ethyl 1 or 2 hydroxypropyl or 1 or 2 hydroxy-butyl group; preferably at least one R' is ROH, but may be for example a methyl, ethyl, propyl, iso propyl, or n- sec-,iso- or tert-butyl group. X may be a monovalent anion such as a chloride or bromide, or an organic carboxylate, e.g. an alkane carboxylate, preferably of 2-5 carbon atoms such as acetate, bisulphite or bisulphate or an organic sulphonate such as methosulphate or a benzene, toluene or xylene sulphonate or a dihydrogen phosphate, or a divalent anion such as sulphate or sulphite or monohydrogen phosphate or a trivalent group such as phosphate or organic carboxylates with 2 or more carboxyl groups such as citrate. The phosphorus compound may also be a phosphine oxide.

The phosphorus compound may alternatively contain 2 or more phosphorus atoms, so long as the phosphorus compound is water soluble to a concentration of at least 0.5 g/l at 25° C. Such phosphorus compounds contain at least 1 hydroxy alkyl group, usually per phosphorus atom, and preferably at least 2 hydroxyalkyl groups per phosphorus atom. Such hydroxyalkyl groups are preferably of formula ROH, where R is as defined above. The group or groups joining the phosphorus atoms together may of formula —R—, —R—O—, —R—O—R— or —R—NH—R or —R—R"—R— where R is as defined above and R" is the residue formed by removal of two hydrogen atoms, bonded to nitrogen, from a di or polyamide or di or poly amine, such as urea, dicyandiamidae, thiourea or guanidine. Such compounds with 2 or more, e.g. 3, hydroxyalkyl groups per phosphorus atom may be made by self condensation of compounds with 3 or 4 hydroxyalkyl groups attached to one phosphorus atom, e.g. of formula $[HOR\ P\ R'_nO_m]_yX_x$ or with a compound of formula $R"H_2$ such as urea. The condensation can be performed by heating at 40°–120° C.

Preferably the phosphorus compound contains only one phosphorus atom and 3 or 4 hydroxyalkyl groups especially hydroxymethyl groups. Such compounds are made by reacting phosphine with an aldehyde usually formaldehyde or a ketone in the presence of mineral acid usually hydrochloric, sulphuric or phosphoric acid. Depending on the proportions the product may be a tris hydroxyalkyl phosphine or tetra kis (hydroxyalkyl) phosphonium salt; however, the latter tends to be converted to the former under aqueous alkaline conditions with small smounts of the dimeric compound with 2 phosphorus atoms and an ROR bridge and/or the phosphine oxide with n=2, m=1, x=0. The product may contain up to 10% by weight of free aldehyde or ketone, e.g. formaldehyde and up to 10% by weight of acid. The phosphorus compound usually has a pH of 1–6, when in 75% by weight aqueous solution. The phosphorus compounds in which one or more of $R_1$ are alkyl groups are made from the corresponding alkyl substituted phosphines by reaction with the aldehyde or ketone. To avoid foaming we prefer that any alkyl or alkenyl groups present should have less than 5 carbon atoms. However compounds in which 1 or 2 alkyl or alkenyl groups per molecule have up to 24 carbon atoms are effective biocides and may be used according to our invention in applications where foaming does not present a problem.

Thus specific examples of biocides according to our invention include tetrakis (hydroxymethyl) phosphonium sulphate, tetrakis (hydroxymethyl) phosphonium chloride, tetrakis (hydroxymethyl) phosphonium phosphate and tris (hydroxymethyl) phosphine oxide as preferred examples and dodecyl tris (hydroxymethyl) phosphonium chloride or oleyl tris (hydroxymethyl) phosphonium sulphate as less preferred examples.

The phosphorus compound may be added to the water to be treated in an amount effective to inhibit growth of the microorganisms therein. The amount is usually 1–5000, e.g. 1–1000, preferably 5–150 and especially 20–50 parts by weight of compound per million parts by weight of the water. For instance we prefer to add 0.6–700, preferably 3–100 and especially 10–30 parts by weight of tetrakis (hydroxymethyl) phosphonium group per million parts of water, or or 0.4–400 preferably 2–60 and especially 8–20 parts by weight of hydroxy alkyl groups (especially hydroxymethyl groups) bonded to phosphorus per million parts of water.

The phosphorus compound may be added in aqueous solution to the water. The pH of the water after treatment is usually 5-10, e.g. 6-9, typically 6-7 or 7.5-9.

There may also be added to the water, scale or corrosion inhibitors, e.g. phosphonates (including aminomethylene phosphonates), polymaleates, polyacrylates, polymethacrylates, polyphosphates or phosphate esters as scale inhibitors in conventional amounts or inorganic corrosion inhibitors such as soluble zinc salts, nitrite, or sulphite or organic corrosion inhibitors such as benzoate, phosphonate, tannin, lignin, benzotriazoles or mercapto benztriazoles, all used again in conventional amounts. We prefer that phosphorus compounds in accordance with our invention should not be used in conjunction with chromates. The scale and/or corrosion inhibitors may be added to the water separately from or in association with the phosphorus compound. There may be added to the water to be treated oxygen scavengers flocculants such as polyacrylamide, dispersants, anti foams such as silicones or polyethylenoxylated antifoams or other biocides such as tin compounds or isothiazolones.

The present invention also provides a composition for treating water containing aquatic microorganisms, which comprises a phosphorus compound containing at least one hydroxyalkyl group attached to a phosphorus atom, together with one or more other biocides, and/or scale or corrosion inhibitors, oxygen scavengers, flocculants, dispersants, and/or antifoam. Compositions of the invention may contain other biocides in addition to the phosphorus compound.

The microorganisms to be treated are usually bacteria, fungi, yeasts and algae that grow in aquatic environments. Included in this classification are sulphate reducing bacteria, e.g. Desulphovibrio, iron bacteria e.g. Gallionella and slime forming bacteria, e.g. Pseudomonas, which last are particularly troublesome in aqueous systems. The water to be treated may be industrial cooling water, e.g. for power stations or chemical plants or for steel or paper or brewing and may be used in closed circuit or in open circuit involving evaporation in cooling towers. Alternatively, the water may be process water, especially process water containing significant sources of nutrients for microorganisms such as process water for paper making plants and breweries. Injection water for oil fields or water used in reverse osmosis plants e.g. to provide industrial processes or boiler feed water, may be treated.

The process is also applicable to the treatment of geothermal water, water in domestic, industrial and institutional central heating and air conditioning systems and water used for hydrostatic testing of pipelines and vessels, swimming baths and as cooling water for ships and marine engines.

The invention is also applicable to the control of microbial contamination in a wide variety of aqueous based products. For example the hydroxy alkyl phosphorus compounds may be added to a variety of solutions and emulsion compositions such as paints, cutting oils, bitumen and tar emulsions, adhesives, weedkillers and insecticides, as well as to solid or concentrated compositions for addition to water in the preparation of such products. The invention, therefore, further provides aqueous based products which are subject to microbial spoilage to which has been added a bacteriostatic or bactericidal quantity of a phosphorus compound containing at least one hydroxyalkyl group attached to the phosphorus atom. Typically such compositions consist of aqueous solutions, suspensions or emulsions of at least one functional ingredient together with a minor proportion of a phosphorus compound of the invention, sufficient to inhibit growth of microorganisms therein.

The systems to which the invention is particularly applicable are those involving the circulation or storage of substantial quantities of water under conditions favouring the multiplication of bacteria, especially hardy bacteria such as *P aeruginosa*, e.g. conditions involving maintaining or periodically raising the water to super ambient temperatures favouring bacterial proliferation, or maintaining nutrients for the bacteria in the water systems.

The invention is illustrated in the following Examples, in which a phosphorus compound was compared for activity against formaldehyde and a control. The phosphorus compound, unless stated to the contrary, was a 75% by weight aqueous solution of tetrakis (hydroxymethyl) phosphonium sulphate which solution is referred to herein as THPS and which contained 0.4% free formaldehyde and had a pH of 4. The formaldehyde comparison was used in 40% aqueous solution. All dosages are expressed in parts per million by weight of the aqueous biocide solution based on the weight of water treated, unless otherwise stated.

EXAMPLE 1

Activity Against *Pseudomonas aeruginosa*

A freeze dried monoculture of *Pseudomonas aeruginosa* (NC1B 8295 supplied by the Torrey research station was incubated in nutrient broth for about 24 hours at 30° C. till turbid. Two consecutive subcultures were then carried out to ensure that the bacteria were in a state of active growth. 2 ml of the final broth was added to 500 ml sterile, 0.25 strength Ringer solution and evenly dispersed. The innoculated solution was incubated at 30° C. for 24 hrs to give a standard test medium containing $10^8$ bacteria per ml.

The test medium was divided into 50 ml portions. One portion was kept as a control and the other portions were dosed with various levels of THPS solution and, for comparative data, a proprietary, isothiazolone based biocide. After incubating for 16 hours at room temperature, the bacterial levels in each portion were measured by a standard plate count procedure. The results were as follows:

| BIOCIDE CONCENTRATION (ppm) | SURVIVING BACTERIA PER ml | |
|---|---|---|
| | THPS solution | Proprietary isothiazolone based biocide |
| 0 | $10^8$ | $10^8$ |
| 20 | $5 \times 10^3$ | $10^7$ |
| 30 | 600 | $10^7$ |
| 40 | 60 | $10^6$ |
| 50 | 0 | $10^5$ |

It is therefore demonstrated that THPS is extremely effective against *Pseudomonas aeruginosa* and, in fact, gives a better performance, in this test, than the proprietary isothiazolone based product.

EXAMPLE 2

Activity Against Cooling Water Bacteria

A sample of recirculating water from a heavily infected industrial cooling system was used as a source of micro-organisms for this test. The microbiological population was found to be mixed but the predominant organism was a gram negative rod-shaped bacterium, not specifically identified.

A test medium, containing over $10^7$ bacteria per ml, was made up by mixing the infected cooling water, as above, with tap water from South Staffordshire, England, previously dechlorinated by the addition of a small excess of sodium thiosulphate. The test medium was divided into 50 ml portions and one portion was kept as a control. The other portions were dosed with various levels of THPS. After incubating for 16 hours at room temperature the bacterial levels in each portion were measured by a standard plate count procedure. The results were as follows:

| THPS DOSE LEVEL (ppm) | SURVIVING BACTERIA PER ml. |
|---|---|
| 0 | $10^7$ |
| 10 | $10^6$ |
| 20 | $2 \times 10^3$ |
| 30 | 150 |
| 50 | 20 |
| 100 | 0 |

It is therefore demonstrated that bacteria from an industrial cooling water system were effectively killed by THPS.

COMPARATIVE EXAMPLE

Comparison With Formaldehyde

Since it was known that, under certain conditions, THPS could slowly react with water to form formaldehyde it was necessary to prove that the formaldehyde was not the agent responsible for killing the bacteria. Hence, at the same time that the procedure described in example 2 was carried out, similar tests, using the same test medium, were carried out using formaldehyde. The results were as follows:

| FORMALDEHYDE DOSE LEVEL (ppm) | SURVIVING BACTERIA PER ml. |
|---|---|
| 0 | $10^7$ |
| 0.1 | $10^7$ |
| 0.5 | $10^6$ |
| 1.0 | $10^6$ |
| 5.0 | $10^6$ |

Theoretically 30 ppm of THPS, if completely reacted with water, would yield 3.3 ppm of formaldehyde. Since we have shown (see results table of example 2) that 30 ppm of THPS reduced the bacterial population from $10^7$ to 150 per ml and that (from table above) even 5 ppm of formaldehyde only gave a slight reduction in the bacterial population it is concluded that the bactericidal activity of THPS is not solely due to released formaldehyde.

EXAMPLE 3

Effect of pH

This series of tests was conducted to demonstrate the microbiocidal activity of THPS over the range of pH values commonly found in cooling water systems.

A sample of recirculating water from a heavily infected industrial cooling water system was used as a source of micro-organisms for this test. The microbiological population was found to be mixed but the predominant organism was identified as *Bacillus cereus*.

A few ml of the infected recirculating water was added to nutrient broth which was then incubated for about 24 hours at 30° C. till turbid. 10 ml of the broth was then added to 5 liters of tap water from South Staffordshire, England, previously dechlorinated with a small excess of sodium thiosulphate. This suspension of bacteria was used as the test medium.

The test medium was divided into 50 ml portions four of which were kept as controls. The pH values of the four controls were adjusted, by dropwise addition of 0.1N sodium hydroxide solution or 0.1N hydrochloric acid to the required values.

For the other portions, each was dosed with the appropriate level of THPS and its pH was quickly adjusted to the required value. All of the portions of test medium were incubated at 30° C. for 19 hours. The bacterial levels were then measured by a standard plate count procedure. The results were as follows:

| THPS DOSE LEVEL (ppm) | SOLUTION pH VALUE | SURVIVING BACTERIA PER ML |
|---|---|---|
| 0 | 6 | $10^7$ |
| 25 | 6 | $10^5$ |
| 50 | 6 | $10^3$ |
| 100 | 6 | 230 |
| 200 | 6 | 0 |
| 0 | 7 | $10^7$ |
| 25 | 7 | $10^4$ |
| 50 | 7 | 350 |
| 100 | 7 | 150 |
| 0 | 8 | $10^7$ |
| 25 | 8 | $10^5$ |
| 50 | 8 | 500 |
| 100 | 8 | 160 |
| 0 | 9 | $10^7$ |
| 25 | 9 | $10^5$ |
| 50 | 9 | 500 |
| 100 | 9 | 170 |
| 200 | 9 | 60 |

It is thus demonstrated that THPS is fully effective as a bactericide over the full range of pH values commonly found in cooling water systems.

EXAMPLE 4

Activity Against Algae

A batch of tap water from South Staffordshire, England, was dechlorinated by the addition of a small excess of sodium thiosulphate. 50 ml portions of the water were measured into each of two screw capped glass jars and each portion was innoculated with a mixed culture of unicellular and filamentous algae. One jar was dosed with 150 ppm THPS solution and one left untreated as a control. Both jars were capped and exposed to light for 7 days. At the end of this period there was a mass of green, growing algae in the untreated jar but no living algae could be detected in the treated jar.

EXAMPLE 5

Plant Trial 1

A full scale trial was carried out on an industrial open, evaporative cooling system with the following parameters:
(a) System capacity: 22,000 gallons
(b) Recirculation rate: 72,000 gallons/hr
(c) Cooling towers: 4×induced draught
(d) Temperature drop: 6° C.
(e) Concentration factor: 1.5

The cooling system was in continuous use and immediately prior to the trial the bacteria level in the recirculating water as measured by a standard plate count procedure, was about $10^6$ per ml. A shot dose of 120 ppm THPS solution was added to the system water and after 3 hours the bacterial level in the recirculating water had fallen to about 200 per ml. No problem with foaming was experienced.

This example illustrates the effectiveness of THPS as a bactericide in a large industrial cooling system.

EXAMPLE 6

Plant Trial 2

A further scale trial was carried out on a second industrial open, evaporative cooling system. System parameters are as follows:
(a) System capacity: 10,000 gallons
(b) Recirculation rate: 100,000 gallons/hr
(c) Cooling towers: 3×forced draught
(d) Temperature drop: 5° C.
(e) Concentration factor: 2

The cooling system was in continuous use and immediately prior to the trial the bacterial level in the recirculating water, as measured by a standard plate count procedure, was 2000 per ml. A shot dose of 96 ppm THPS solution was added to the system water and within 1 hour the bacterial level had been reduced to 100 per ml. No problem with foaming was experienced.

This example further illustrates the effectiveness of THPS as a bactericide in an industrial cooling water system.

EXAMPLE 7

Bactericidal Activities of other THP Salts

THPC (tetrakishydroxymethyl phosphonium chloride) (added as an 80% by weight aqueous solution) and THPP (tetrakishydroxymethyl phosphonium phosphate) (added in aqueous solution containing a concentration of tetrakis(hydroxymethyl) phosphonium group equivalent to 750 g tri[tetrakis(hydroxymethyl)phosphonium] phosphate per kg of solution) were tested for activity against Pseudomonas aeruginosa according to the test method described in Example 1. Results were as follows:

| BIOCIDE CONCENTRATION (ppm) of aqueous biocide solution added | SURVIVING BACTERIA PER ML | | |
|---|---|---|---|
| | THPS-75 (Ex 1) | THPC-80 | THPP-75 |
| 0 | $10^8$ | $10^8$ | $10^8$ |
| 20 | $5 \times 10^3$ | 530 | $10^3$ |
| 30 | 600 | 170 | 920 |
| 40 | 60 | 60 | 30 |
| 50 | 0 | 20 | 0 |
| 100 | — | 0 | 0 |

It is therefore demonstrated that the chloride and phosphate salts of the THP moiety are at least as effective as biocides as THPS against cooling water bacteria at pH 6.6

EXAMPLE 8

Liquid Scourer Formulation

A liquid scourer formulation was made up according to the following recipe:

| COMPONENT | % W/W |
|---|---|
| Synthetic Clay (Laponite B ®, Laporte Industries, England) | 0.67 |
| Gum Arabic | 0.04 |
| Fatty Acid Diethanolamide (sold under Trade Mark EMPILAN CDE ®, by Albright & Wilson, England) | 2.30 |
| Heavy Calcium Carbonate | 30.09 |
| Water | 66.90 |

An active culture of Pseudomonas aeruginosa was made up in nutrient broth as described in Example 1. 0.2 ml of the final sub-cultured broth was added to 50 ml of the above formulation to give a bacterial concentration of approximately 108 per ml. The infected formulation was divided into three equal portions, the first portion was used as a control (i.e. no biocide added) and to the second and third portions THPS-75 (i.e the 75% aqueous solution of THPS used in Example 1) was added to give levels of 500 ppm and 1,000 ppm, in the formulation, respectively.

All three portions were incubated at 30° C. for 16 hours and the bacterial levels in such portion was measured by a standard plate count procedure. The results were as follows:

| THPS-75 CONCENTRATION (ppm) | SURVIVING BACTERIA PER ML |
|---|---|
| 0 | 2,500 |
| 500 | 0 |
| 1000 | 0 |

EXAMPLE 9

Detergent Formulation

A liquid detergent formulation was made-up according to the following recipe:

| COMPONENT | % W/W |
|---|---|
| Nonyl Phenol Ethoxylate (sold under the Trade Mark EMPILAN NP9 ® by Albright & Wilson, England) | 10 |
| Water | 90 |

The bactericidal test procedure in Example 8 was repeated using this formulation and results were as follows:

| THPS-75 CONCENTRATION (ppm) | SURVIVING BACTERIA PER ML |
|---|---|
| 0 | $10^8$ |
| 500 | 0 |
| 1000 | 0 |

EXAMPLE 10

Adhesive Paste Formulation

An adhesive paste formulation was made up according to the following recipe:

| COMPONENT | % W/W |
|---|---|
| Sodium Carboxymethylcellulose | 3 |

-continued

| COMPONENT | % W/W |
|---|---|
| (Courlose ®, Courtaulds Ltd, England). | |
| Water | 97 |

The bastericidal test procedure described in Example 8 was repeated using this formulation and results were as follows:

| THPS-75 CONCENTRATION (ppm) | SURVIVING BACTERIA PER ML |
|---|---|
| 0 | 1,500 |
| 500 | 0 |
| 1000 | 0 |

EXAMPLE 11

Dispersant Formulation

A dispersant formulation was made up according to the following recipe:

| COMPONENT | % W/W |
|---|---|
| Sodium Ligninsulphonate (Borresperse NA ®, Borregaard, Norway) | 5 |
| Water | 95 |

The biocidal test procedure described in Example 8 was repeated using this formulation and the results were as follows:

| THPS-75 CONCENTRATION (ppm) | SURVIVING BACTERIA PER ML |
|---|---|
| 0 | $10^8$ |
| 500 | $5 \times 10^3$ |
| 1000 | 10 |
| 1,500 | 0 |

The above Examples 8–11 demonstrate the effectiveness of the compounds of the present invention as biocides for use in aqueous base formulations.

EXAMPLE 12

Oxygen Scavenging Activity

The compounds of the present invention have the capacity to react with dissolved oxygen as shown by the following experiments:

1 liter of aerated deionised water was charged to a sealed glass vessel fitted with a stirrer and an oxygen electrode (Model 1511, EIL Limited, England). A readout of the dissolved oxygen level in the water was provided by a model 1510 dissolved oxygen meter (EIL, England) and an X/Y recorder.

The experiment was set up at 25° C. and 0.1N sodium hydroxide solution was added in a sufficient quantity so that when 500 ppm of THPS-75 was subsequently added, the solution pH was about 9.

At the time of addition of the THPS-75 the dissolved oxygen level was about 10 ppm and the rate of reaction of scavenger with dissolved oxygen at pH 9 was very slow. However, on reducing the pH to below 7, by the addition of 0.1N hydrochloric acid, the reaction rate increased. When the pH was 6.2, the concentration of dissolved oxygen in the water was reduced from 10 ppm to zero ppm in 50 seconds.

COMPARATIVE EXAMPLE B

Activity of a Long Chain Alkyl Phosphonium Salt

Simultaneously with the experiment described in Example 2, a similar experiment was carried out using the same test medium, to assess the activity of lauryltributyl phosphonium chloride (LTBPC) as a bactericide.

For convenience, the results have been expressed in terms of a 75% solution of LTBPC to enable a direct comparison of the activity of LTBPC and THPS to be made:

| LTBPC CONCENTRATION (ppm) | SURVIVING BACTERIA PER ML |
|---|---|
| 0 | $10^7$ |
| 13.3 | $10^6$ |
| 26.7 | $10^5$ |

From these results and the ones given in Example 2 it can be seen that on a weight-for-weight basis, THPS is more effective than LTBPC as a bactericide against cooling water bacteria.

COMPARATIVE EXAMPLE C

Activity of other Alkyl Phosphonium Salts

A small range of other alkyl phosphonium salts was tested against cooling water bacteria according to the method given in Example 2. Those tested were:

Triphenylmethyl phosphonium chloride
Tributylbenzyl phosphonium chloride
Tributyl-3, 4-dichlorobenzyl phosphonium chloride
Tributylmethyl phosphonium chloride All of these compounds were found to be totally inactive, even up to a level of 200 ppm.

These examples demonstrate that without a hydroxyalkyl group attached to the central phosphorus atom, short chain phosphonium salts tend to be inactive as bactericides against cooling water bacteria.

EXAMPLE 13

Activity Against Fungi

Fungal spores, isolated from an industrial cooling water system were used in this test. The variety of fungus was not specifically identified, but was thought to be of the genus Aspergillus.

50 ml portions of infected water were prepared. One was left untreated as a control and the others were treated with THPS 75 at 100 and 200 ppm. The portions of water were incubated at 30° C. for 5 days and the degree of fungal infection measured by a standard plate count technique.

Results were as follows:

| THPS 75 CONCENTRATION (ppm) | SURVIVING FUNGAL STORES PER ML |
|---|---|
| 0 | 500 |
| 100 | 500 |
| 200 | 50 |

It is thus demonstrated that the THP moeity is an active fungicide.

Other aquatic environments which may be treated with the hydroxyalkyl phosphorus compounds according to the method of the invention are cooling or process water in board mills, fertilizer manufacture, oil refineries, primary metals manufacture, e.g. steel or copper, petrochemicals, rubber manufacture, textile and fabrics industries, industrial gas manufacture, minerals recovery, glass and ceramic manufacture, food industry, leather manufacture, heavy and light engineering, including metal fabrication and automotive engineering, furniture manufacture, electronics industry and surface coatings and adhesives manufacture, and other manufacturing industries.

We claim:

1. A method for treating a water system susceptable to infection by aquatic microorganisms in order to inhibit the growth of the latter, which method comprises adding to said water system at least one phosphorus compound selected from the group consisting of: compounds which have the formula $(HORPR'_3)yX$ wherein y is equal to the valvency of X; R is an alkylene group of 1 to 4 carbon atoms; each R' is separately selected from the groups consisting of alkyl and alkenyl groups having up to 4 carbon atoms and groups of the formula HOR—, wherein R is as defined above; and X is an anion such that the phosphorus compound is water soluble; and condensates thereof; said phosphorus compound being added in a quantity at least sufficient to inhibit the growth of mocroorganisms in said water systems.

2. The method according to claim 1 wherein each R' is an HOR-group.

3. The method according to claim 2 wherein each R is a methylene group.

4. The method according to claim 1 wherein said phosphorus compound is selected from the group consisting of tetrakis (hydroxy methyl) phosphonium sulphate, tetrakis (hydroxy methyl) phosphonium chloride and tetrakis (hydroxy methyl) phosphonium phosphate.

5. The method according to claim 1 wherein the phosphorus compound is a compound having at least 2 phosphorus atoms per molecule, which is formed by the condensation of a compound having said formula.

6. The method according to claim 5 wherein the condensation occurs in the presence of a compound selected from the group consisting of urea, dicyandiamide, thiourea and guanidine.

7. The method according to claim 1 wherein the phosphorus compound is added in an amount from 1 to 2,000 parts per million by weight of the water to be treated.

8. The method according to claim 7 wherein the concentration of the phosphorus compound in the water system is maintained between 5 and 150 parts per million by weight.

9. The method according to claim 8 wherein the phosphorus compound is a compound having at least 2 phosphorus atoms per molecule, which is formed by the condensation of a compound having said formula and wherein said condensation occurs in the presence of a compound selected from the group consisting of urea, dicyandiamide, thiourea and guanidine.

10. The method according to claim 1 wherein said water system contains industrial cooling or process water.

11. The method according to claim 10 wherein said cooling water is from a power station, chemical plant, steel or paper mill or brewery.

12. The method according to claim 1 wherein said water system contains injection water for oil fields.

13. The method according to claim 1 wherein said water system contains water selected from geothermal water and water in central heating systems, air conditioning systems, and for use in hydrostatic testing, swimming baths and as cooling water for ships and marine engines.

14. The method according to claim 1 wherein a composition consisting of said at least one phosphorus compound and at least one other water treatment additive selected from scale and corrosion inhibitors, flocculants, dispersants, antifoams, oxygen scavengers and biocides is added to water.

* * * * *